United States Patent [19]

Lucero

[11] Patent Number: 5,658,948

[45] Date of Patent: *Aug. 19, 1997

[54] ENHANCEMENT OF BENZALKONIUM CHLORIDE PRESERVATIVE ACTIVITY IN FORMULATIONS CONTAINING AN INCOMPATIBLE DRUG USING AMINO ACIDS HAVING NET POSITIVE CHARGE

[75] Inventor: Jasmin C. Lucero, Irvine, Calif.

[73] Assignee: Allergan, Waco, Tex.

[*] Notice: The term of this patent shall not extend beyond the expiration date of Pat. No. 5,504,113.

[21] Appl. No.: 579,001

[22] Filed: Dec. 27, 1995

Related U.S. Application Data

[63] Continuation-in-part of Ser. No. 204,853, Mar. 2, 1994, Pat. No. 5,504,113.

[51] Int. Cl.⁶ .......................... A61K 31/205; A61K 31/14
[52] U.S. Cl. .............................................. 514/554; 514/643
[58] Field of Search ...................... 514/554, 643

[56] References Cited

PUBLICATIONS

Chemical Abstracts 110: 219120n, 1989. Fu et al.

*Primary Examiner*—Zohreh Fay
*Attorney, Agent, or Firm*—Walter A. Hackler

[57] ABSTRACT

A formulation and method includes an acceptable drug, such as Prostaglandins, Flurbiprofen, Ketorolac Tromethamine, Cetirizine HCl Indomethacin and Bufrolin, which are interactive with benzalkonium chloride to form a precipitate along with benzalkonium chloride acting as a preservative and an amino acid having enough positive charge at the pH of the formulation and/or Tromethamine present in an amount sufficient to interfere with the interaction between the drug and benzalkonium chloride in order to maintain the preservative activity of the benzalkonium chloride. Further, the use of Lysine, L-arginine, or Histidine is also useful in reducing the cytotoxicity of the formulation.

10 Claims, 1 Drawing Sheet

ENHANCEMENT OF BENZALKONIUM CHLORIDE PRESERVATIVE ACTIVITY IN FORMULATIONS CONTAINING AN INCOMPATIBLE DRUG USING AMINO ACIDS HAVING NET POSITIVE CHARGE

This application is a continuation-in-part of U.S. patent application Ser. No. 204,853, filed Mar. 2, 1994, now U.S. Pat. No. 5,504,113.

The present invention generally relates to improved formulations and solutions and more particularly to improved preservative systems for acceptable drug formulations which have an incompatibility with benzalkonium chloride (BAK) such as Prostaglandins, Flurbiprofen, Ketorolac Tromethamine, Cetirizine HCl and Indomethacin. More specifically, the present invention pertains to the preservative for an ophthalmologically acceptable drug such as Bufrolin having activity for treating seasonal allergies, allergic conjunctivitis, giant papillar conjunctivitis, and vernal keratocojunctivitis.

Ophthalmologically acceptable drug formulations generally contain effective compounds and a number of ophthalmologically acceptable excipients. Such formulations generally include solutions, ointments, and suspensions, etc. The formulations may include excipients such as stabilizing agents, surfactants, buffering systems, chelating systems, viscosity agents, tonicity agents, and, importantly, a preservative.

Ophthalmic formulations, understandably, must be sterile and if a multi-dose regimen is intended, the formulation must be preserved with an effective antimicrobial agent.

As discussed in U.S. Pat. No. 5,110,493, organomercurials have been used extensively as the preservatives in ophthalmic solutions. As reported in this reference, these compounds pose difficulties due to potential mercury toxicity as well as poor chemical stability.

Therefore, benzalkonium chloride, which is a quaternary ammonium compound, has been widely used in ophthalmic solutions. It is also wellknown, however, that benzalkonium chloride is considered incompatible with anionic drugs, forming insoluble complexes which cause the solution to turn cloudy.

This is because of the fact that many anionic drug entities carry a negative charge at physiological pH. In fact, all acidic drug entities will carry a negative charge at all pH's above their pKa's.

In the case of benzalkonium chloride, which is a positively charged preservative, insoluble complexes can be formed with acidic drug entities causing the drug to precipitate out of solution. Concomitant with the removal of the drug from solution is the rimoval of benzalkonium chloride, thereby rendering this quaternary germicide incapable of performing its function as an antimicrobial agent.

Benzalkonium chloride is a mixture of alkylbenzyldimethylammonium chloride of the general formula as shown below in which R represents a mixture of the alkyls from $C_8H_{17}$ to $C_{18}H_{37}$

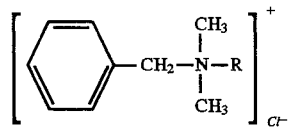

As hereinbefore noted, it is well-known that benzalkonium chloride is generally incompatible with avionic detergents or avionic drug compounds. See U.S. Pat. No. 5,110, 493, and *The Merck Index*, 11th Edition, Merck & Co., Inc., 1989.

The present invention specifically relates to the discovery that an additive having a positive charge at the pH of the formulation can be used to compete with benzalkonium chloride and reduce complexation of any anionic drug with the benzalkonium chloride and thereby enhance the preservative effectiveness of the benzalkonium chloride.

SUMMARY OF THE INVENTION

A formulation in accordance with the present invention generally includes an acceptable drug which is interactive with benzalkonium chloride in combination with the very entity, benzalkonium chloride, with which the acceptable drug forms a complex, thereby removing the benzalkonium chloride from solution, and consequently reducing its effectiveness as a preservative. As noted, the benzalkonium chloride is added as a preservative and is active in that regard. Examples of such drugs include, but not limited to, Prostaglandins, Flurbiprofen, Keterolac Tromethamine, Cetirizine HCl Indomethacin and Bufrolin.

In combination with the acceptable drug and the benzalkonium chloride is an additive, having a net positive charge at the pH of the formulation, and present in amounts sufficient to enhance preservative effectiveness of the benzalkonium chloride. An effective amount is sufficient for the additive to compete with the benzalkonium chloride for the interaction of the ophthalmologically acceptable drug, thereby freeing more benzalkonium chloride and providing overall enhancement of the preservative activity of the benzalkonium chloride.

More particularly, an ophthalmologically acceptable drug may comprise bufrolin and the additive may comprise an amino add having a net positive charge at the pH of the formulation present in sufficient amounts to interfere with the interaction between the drug and the benzalkonium chloride in order to maintain the preservative activity of the benzalkonium chloride.

More particularly, the amino acid may be selected from a group consisting essentially of Lysine, L-arginine and Histidine.

More specifically, the ophthalmic solution in accordance with the present invention includes burrolin as the ophthalmologically acceptable drug and present in an amount of up to about 4% w/v. Preferably, the amino add comprises L-arginine or Lysine or Histidine present in an amount between about 0.5% and about 5% w/v.

Utilization of the L-arginine, Lysine or Histidine reduces the amount of benzalkonium chloride necessary as a preservative and accordingly, in accordance with the present invention, the benzalkonium chloride may be present in an amount about 100 ppm or less.

As an alternative embodiment of the present invention, the additive comprises Tromethamine present in an amount of between about 0.3% and about 2% w/v.

In another embodiment of the present invention, a plurality of additives, each having a net positive charge at the pH of the formulation, are utilized in an mount sufficient to inhibit formation of an insoluble complex between the benzalkonium chloride and the ophthalmologically acceptable drug. More particularly, in this last-mentioned embodiment, the ophthalmologically acceptable drug formulation comprises both an amino acid having a net positive charge at the pH of the formulation and Tromethamine. The amino acid may comprise either Lysine, L-arginine, or Histidine, or combinations thereof.

In addition, the utilization of L-arginine, Lysine or Histidine and Trometharnine together reduces the amount of BAK necessary as a preservative and accordingly, in accordance with the present invention, the BAK may be present in an amount about 100 ppm or less.

BRIEF DESCRIPTION OF THE DRAWINGS

The advantages and features of the present invention will be better understood by the following description when considered in conjunction with the accompanying drawing in which.

DETAILED DESCRIPTION

Figure 1:
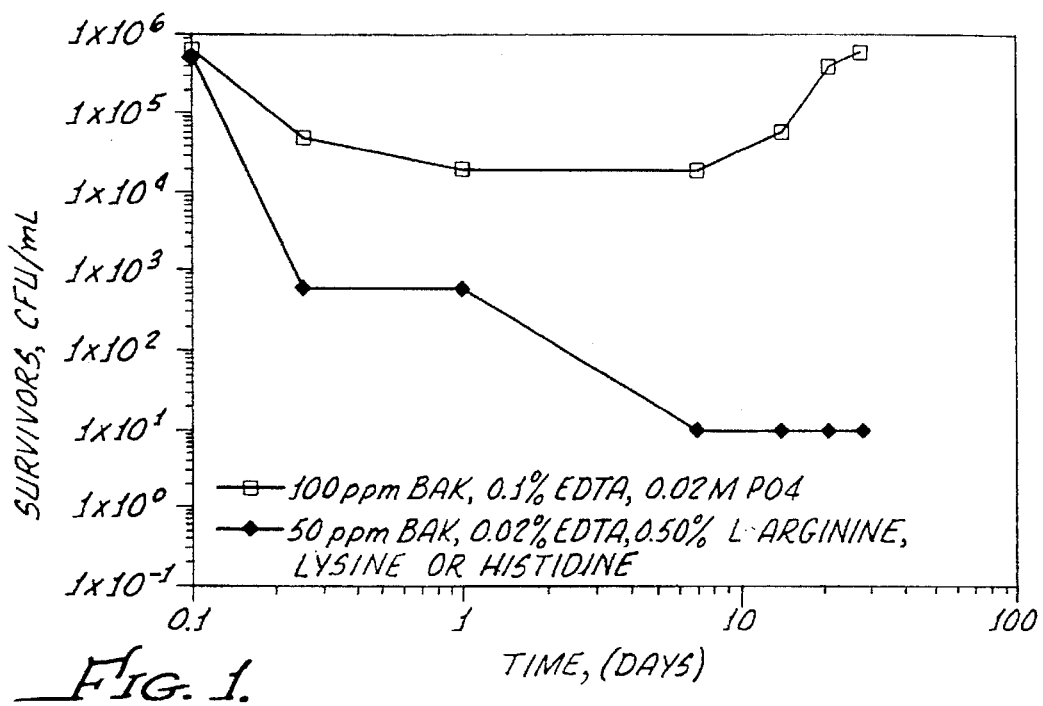
FIG. 1 is a comparison of bacterial (*P. aeruginosa*) recoveries of formulations with and without L-arginine. Lysing or Histidine and Tromethamine.

Bufrolin is a classic example of an artionic drug that forms an insoluble complex with benzalkonium chloride. Bufrolin is 6-n-Butyl-1,4,7,10-tetrahydro-4,10-dioxo-1,7-phenanthroline-2,8-dicarboxylic acid. As hereinabove noted, this drug has activity for treating seasonal allergies, allergic conjunctivitis, giant papillar conjunctivitis and vernal keratoconjunctivitis. It is to be appreciated that while this particular drug is cited throughout here as an example, other artionic drugs that form an insoluble complex with benzalkonium chloride are to be considered to be within the scope of the present invention.

It is also well-known that benzalkoninm chloride (BAK), alone or in combination with disodium edetate (EDTA), has been widely used for many years as an ophthalmic preservative. This preservative, through extensive testing and use, has been proven to be one of the most effective and rapid-acting preservatives which is stable over the pH range which most ophthalmic products are formulated.

It is also known that the addition of between about 0.01% and about 0.1% EDTA increases the effectiveness of BAK against some resistant strains of the pseudomonas species.

Unfortunately, since BAK is a cationic compound, incompatibility with anionic drugs limits its use as a preservative. The synergism expected from the combination of BAK and EDTA has not been successful in preserving formulations having high concentrations of anionic drugs such as Bufrolin which require up to 4% w/v for the treatment of allergic conjunctivitis in phosphate-buffered solutions with a pH between about 6 and about 8, and preferably about 7.4.

Amino acids suitable for use in the present invention having a positive charge at the pH of the formulation may include Lysine, Arginine and Histidine, having positively charged R groups, as shown below with the amino and carboxyl group ionized as they would occur at a pH of about 7.0. These amino acids can be used individually, or in combination with one another and Tromethamine or Tris [2-Amino-2-(hydroxymethyl)-1,3-propanediol], which is a well-known biological buffer.

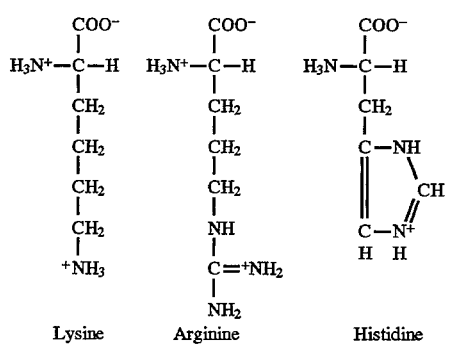

Lysine    Arginine    Histidine

Microbiological studies assessing the preservative efficacy of the formulation made in accordance with the present invention, as well as cytotoxicity tests, have been performed in accordance with the following methods:

| Preservative Efficacy Test |
|---|
| Materials: |
| a. Test Organisms |
|     S. aureus, P. aeruginosa, E. coli, A. niger, C. albicans |
| b. Recovery Media |
|     Trypticase soy broth with neutralizing phosphate buffer and Polysorbate 80 |
|     Trypticase Soy Agar with 1.0% Glucose |
| Method: |
| 1. 10 mL aliquots of the test samples are inoculated with 50 μL of test organisms to yield a final concentration of about 5 $\times$ 10$^6$ CFU/mL. |
| 2. The samples are tested for survivors on D-0, 6 hour, D-1, D-14, D-21, D-28. |

Cytotoxicity—Inulin Permeability Assay

2×10$^5$ MDCK (Madin-Darby Canine Kidney) cells on collagen-coated semi-permeable inserts are incubated for 2 days prior to the assay. 0.4 μCi $^{14}$C-inulin is added to 400 μL of the test sample and 100 μL of this is placed in each insert. At each timepoint, 20 μL of sample is taken from outside of the insert and radioactivity measured using scintillation counting.

The preservative criteria for ophthalmic preparations utilized in the studies include British Pharmacopeia (BP-88), Deutschcs Arzneibuch (DAB-9) and United States Pharmacopeia (USP) as shown in Table I.

TABLE I

Preservative Criteria for Ophthalmic Preparations

| | BP-88 | DAB-9 | USP |
|---|---|---|---|
| S. aureus #6538P | −3 log in 6 hrs<br>0 in 24 hrs | −2 log in 24 hrs<br>−3 log in 7 days | −3 log in 14 days |
| P. aeruginosa #9027 | −3 log in 6 hrs<br>0 in 24 hrs | −2 log in 24 hrs<br>−3 log in 7 days | −3 log in 14 days |
| E. coli #8739 | N/A | N/A | −3 log in 14 days |
| C. albicans #10231 | −2 log in 7 days<br>0 incr. 28 days | −1 log in 14 days | 0 incr. in 14–28 days |
| A. niger #16404 | −2 log in 7 days<br>0 incr. 28 days | −1 log in 14 days | 0 incr. in 14–28 days |

Table II shows the preservative efficacy test results of some formulations:

TABLE II

Preservative Efficacy Test Results of Formulations

| Preservative System | Buffer | DAB-9 | USP |
|---|---|---|---|
| 100 ppm BAK, 0.10% EDTA | 0.02 M PO$_4$ | fail | fail |
| 70 ppm BAK, 0.03% EDTA | 0.10 M Tris | pass | pass |
| 50 ppm BAK, 0.05% EDTA | 0.10 M Tris | fail | fail |
| 50 ppm BAK, 0.02% EDTA, 0.50% L-arginine | 0.10 M Tris | pass | pass |
| 50 ppm BAK, 0.02% EDTA, 0.50% Lysine | 0.10 M Tris | pass | pass |
| 50 ppm BAK, 0.02% EDTA, 0.50% Histidine | 0.10 M Tris | pass | pass |

Sample formulations utilizing L-arginine, Lysine or Histidine include:

Anionic drug—e.g. Bufrolin—4% w/v

Cationic preservative—e.g. BAK

Chelators—e.g. Na$_2$EDTA

Buffers—e.g. tris, phosphate

Salts—e.g. NaCl for tonicity adjustment

Dilute add/base—e.g. HCl/NaOH for pH adjustment

As shown in Table II, the preservative efficacy test (PET) showed that, even with as much as 100 ppm BAK and 0.1% EDTA in 0.02M phosphate buffer (pH 7.4), the 4% w/v Bufrolin formulation failed to meet the USP criteria.

The use of Tris (Tromethamine) as a buffer and counterion enhanced the efficacy of the BAK/EDTA combination and a formulation of 4% w/v Bufrolin with 70 ppm BAK, 0.03% EDTA, and 0.1M Tris pass the DAB-9 test, which is a more stringent criterion than that of the USP.

The addition of Lysine, L-arginine or Histidine further improves the activity of BAK. With as low as 0.5% w/v L-arginine, Lysine or Histidine in combination with 0.10M Tris buffer, the formulation passed DAB-9 with only 50 ppm BAK and 0.02% EDTA with a much better P. aeruginosa kill profile, as shown in FIG. 1. Thus, it is shown in accordance with the present invention that the combination of L-arginine, Lysine or Histidine and Tris lowers the amount of BAK necessary to preserve the resulting formulation.

Figure 2:
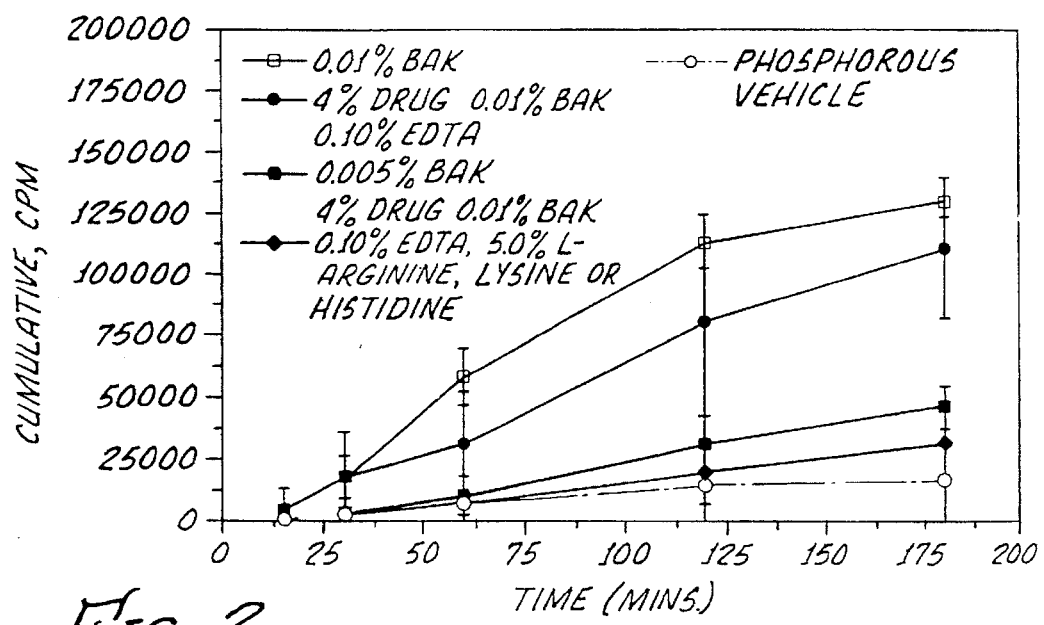
FIG. 2 is a comparison of halin permeability (cytotoxicity) of formulations with and without L-arginine, Lysine or Histidine.

In the inulin permeation test, FIG. 2, the presence of L-arginine, Lysine or Histidine in the formulation significantly decreased the permeability (cytotoxicity) to tight junctions between the epithelial cells by approximately 4.5-fold in comparison to other formulations.

Thus, as shown in FIG. 2, formulations containing 100 ppm BAK, 0.1% EDTA, and 5% L-arginine, Lysine or Histidine have less permeability (less cytotoxicity) than the 50 ppm BAK control.

In accordance with the present invention, the addition of an amino acid, having a net positive charge at about neutral pH, such as Lysine, L-arginine, and Histidine, along with Tris, compete with and prevent BAK from complexing with an anionic drug such as Bufrolin. Thus, the amino acid and/or the Tris are effective in maintaining a stable and adequately preserved formulation. In addition, the presence of an amino acid having a net positive charge at 7.4 pH, such as L-arginine, greatly decreases the cytotoxicity of the formulation.

It should be noted that the effectiveness of the formulation is well within about 5 to about 7.6 pH, generally accepted for ophthalmic formulations, with an ideal pH of about 7.4 for comfort in use of the formulation. Also, while it is preferable to maintain the concentraion of BAK below 100 ppm, such as—for example—25 ppm, 50 ppm, or 75 ppm, formulations may be effective with higher amounts of BAK corresponding to greater amounts of Tris, L-arginine Lysine or Histidine of more than about 4%.

Although there has been hereinabove described a specific ophthalmic solution and method in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A formulation comprising:

a drug interactive with benzalkonium chloride;

benzalkonium chloride active as a preservative; and an amino acid having a net positive charge at the pH of the formulation at a Ph of between about 5 and about 7.6 and present in an amount sufficient to interfere with the interaction between the drug and benzalkonium chloride in order to maintain the preservative activity of the benzalkonium chloride.

2. The formulation according to claim 1 wherein the drug is selected from a group consisting essentially of Prostaglandins, Flurbiprofen, Keterolac Tromethamine, Cetirizine HCl and Indomethacin.

3. The formulation according to claim 1 wherein said drug comprises Bufrolin.

4. The ophthalmic formulation according to claim 1 wherein said amino acid is selected from a group consisting essentially of Lysine and Histidine.

5. The ophthalmic formulation according to claim 1 wherein the drug comprises Bufrolin present in an amount up to about 4% w/v.

6. The ophthalmic formulation according to claim 3 wherein the amino acid comprises Lysine.

7. The formulation according to claim 3 wherein the amino acid comprises Histidine.

8. The formulation according to claim 6 wherein the Lysine is present in an amount of between about 0.5% and about 5% w/v.

9. The formulation according to claim 7 wherein the Histidine is present in an amount of between 0.5% and about 5% w/v.

10. The formulation according to claim 9 wherein the benzalkonium chloride is present in an amount less than about 100 ppm.

* * * * *